(12) United States Patent
Aubrun et al.

(10) Patent No.: US 10,702,462 B2
(45) Date of Patent: Jul. 7, 2020

(54) OIL-IN-WATER EMULSION COMPRISING AT LEAST ONE SPECIFIC MIXTURE OF NONIONIC SURFACTANTS, A WAX COMPRISING AT LEAST ONE ESTER AND A WATER-SOLUBLE POLYSACCHARIDE

(71) Applicant: L'OREAL, Paris (FR)

(72) Inventors: Odile Aubrun, Antony (FR); Fabrice Springinsfeld, Fresnes (FR)

(73) Assignee: L'OREAL, Paris (FR)

( * ) Notice: Subject to any disclaimer, the term of this patent is extended or adjusted under 35 U.S.C. 154(b) by 605 days.

(21) Appl. No.: 14/769,248

(22) PCT Filed: Feb. 14, 2014

(86) PCT No.: PCT/EP2014/052925
§ 371 (c)(1),
(2) Date: Aug. 20, 2015

(87) PCT Pub. No.: WO2014/128060
PCT Pub. Date: Aug. 28, 2014

(65) Prior Publication Data
US 2016/0000665 A1 Jan. 7, 2016

Related U.S. Application Data

(60) Provisional application No. 61/768,941, filed on Feb. 25, 2013.

(30) Foreign Application Priority Data

Feb. 21, 2013 (FR) ..................................... 13 51478

(51) Int. Cl.
| | |
|---|---|
| *A61K 8/26* | (2006.01) |
| *A61K 8/34* | (2006.01) |
| *A61K 8/37* | (2006.01) |
| *A61Q 15/00* | (2006.01) |
| *A61K 8/73* | (2006.01) |
| *A61K 8/92* | (2006.01) |
| *A61K 8/06* | (2006.01) |
| *A45D 34/04* | (2006.01) |

(Continued)

(52) U.S. Cl.
CPC ................ *A61K 8/26* (2013.01); *A45D 34/04* (2013.01); *A61K 8/062* (2013.01); *A61K 8/342* (2013.01); *A61K 8/37* (2013.01); *A61K 8/602* (2013.01); *A61K 8/604* (2013.01); *A61K 8/732* (2013.01); *A61K 8/86* (2013.01); *A61K 8/891* (2013.01); *A61K 8/922* (2013.01); *A61K 8/927* (2013.01); *A61Q 15/00* (2013.01); *A45D 2200/056* (2013.01); *A61K 2800/5422* (2013.01); *A61K 2800/596* (2013.01)

(58) Field of Classification Search
CPC .. A61K 8/342; A61K 2800/596; A61K 8/604; A61K 8/732; A61K 8/922; A61K 8/927; A61K 8/062; A61K 8/86; A61K 8/602; A61K 8/26; A61K 2800/5422; A61K 8/891; A61K 8/37; A61Q 15/00; A45D 34/04; A45D 2200/056

See application file for complete search history.

(56) References Cited

FOREIGN PATENT DOCUMENTS

| | | |
|---|---|---|
| DE | 19962878 A1 | 6/2001 |
| DE | 102006020382 A1 | 10/2007 |

(Continued)

OTHER PUBLICATIONS

"Candelilla Wax", Food and Agriculture Organization of the United Nation, Jan. 1, 2005.

*Primary Examiner* — Robert S Cabral
(74) *Attorney, Agent, or Firm* — Polsinelli PC

(57) ABSTRACT

The present invention relates to a composition in the form of an oil-in-water emulsion, comprising, in a cosmetically acceptable medium: A) a continuous aqueous phase and B) an oily phase dispersed in the said aqueous phase and comprising at least one hydrocarbon-based oil; C) at least one mixture consisting of: i) at least one nonionic surfactant containing a saturated linear hydrocarbon-based chain comprising at least 16 carbon atoms, the said surfactant being other than a fatty alcohol, and ii) at least one fatty alcohol in pure form containing at least 16 carbon atoms or a mixture consisting exclusively of fatty alcohols containing at least 16 carbon atoms; D) at least one wax with a melting point of greater than 45° C. comprising one or more $C_{40}$-$C_{70}$ ester compounds and not comprising any $C_{20}$-$C_{39}$ ester compounds, in an amount from 1 to 10% by weight relative to the total weight of the composition and E) at least one water-soluble polysaccharide; the said composition having a viscosity, measured at 25° C. with a Rheomat RM 180 viscometer at 200 $s^{-1}$ at room temperature with a No. 3 or No. 4 spindle after 10 minutes, ranging from 1500 mPa·s to 12 000 mPa·s and preferably from 2000 mPa·s to 8000 mPa·s. The present invention also relates to a cosmetic process for treating and/or caring for human keratin materials, characterized in that it consists in applying to the surface of the keratin material a composition as defined previously. The present invention also relates to a cosmetic process for treating human perspiration and/or perspiration-related body odour, which consists in applying to the surface of a human keratin material a composition as defined previously comprising at least one deodorant active agent and/or one antiperspirant active agent.

21 Claims, 4 Drawing Sheets

(51) Int. Cl.
*A61K 8/60* (2006.01)
*A61K 8/86* (2006.01)
*A61K 8/891* (2006.01)

(56) References Cited

FOREIGN PATENT DOCUMENTS

| | | |
|---|---|---|
| EP | 1584330 A1 | 10/2005 |
| EP | 2095808 A1 | 9/2009 |
| EP | 2436369 A1 | 4/2012 |
| FR | 2960150 A1 | 11/2011 |
| WO | WO-98/51185 A1 | 11/1998 |
| WO | WO-2010/115973 A1 | 10/2010 |

OIL-IN-WATER EMULSION COMPRISING AT LEAST ONE SPECIFIC MIXTURE OF NONIONIC SURFACTANTS, A WAX COMPRISING AT LEAST ONE ESTER AND A WATER-SOLUBLE POLYSACCHARIDE

CROSS REFERENCE TO RELATED APPLICATIONS

This application is a National Phase filing under 35 U.S.C. § 371 of PCT/EP2014/052925 filed on Feb. 14, 2014; and this application claims priority to Application No. 1351478 filed in France on Feb. 21, 2013; and this application claims the benefit of U.S. Provisional Application No. 61/768,941 filed on Feb. 25, 2013. The entire contents of each application are hereby incorporated by reference.

The present invention relates to a composition in the form of an oil-in-water emulsion, comprising, in a cosmetically acceptable medium:

A) a continuous aqueous phase and

B) an oily phase dispersed in the said aqueous phase and comprising at least one hydrocarbon-based oil;

C) at least one mixture consisting of:

(i) at least one nonionic surfactant containing a saturated linear hydrocarbon-based chain comprising at least 16 carbon atoms, the said surfactant being other than a fatty alcohol, and ii) at least one fatty alcohol in pure form containing at least 16 carbon atoms or a mixture consisting exclusively of fatty alcohols containing at least 16 carbon atoms;

D) at least one wax with a melting point of greater than 45° C. comprising one or more $C_{40}$-$C_{70}$ ester compounds and not comprising any $C_{20}$-$C_{39}$ ester compounds, in an amount from 1 to 10% by weight relative to the total weight of the composition and E) at least one water-soluble polysaccharide; the said composition having a viscosity, measured at 25° C. with a Rheomat RM 180 viscometer at 200 s$^{-1}$ at room temperature with a No. 3 or No. 4 spindle after 10 minutes, ranging from 1500 mPa·s to 12 000 mPa·s and preferably from 2000 mPa·s to 8000 mPa·s.

The present invention also relates to a cosmetic process for treating and/or caring for human keratin materials, characterized in that it consists in applying to the surface of the keratin material at least one composition as defined previously.

In the field of cosmetic skincare products, especially deodorant and antiperspirant products, various galenical categories may be defined: aerosols, sticks, creams, gels, soft solids, roll-ons.

Roll-ons are a galenical form strongly represented on the market, but, like systems in direct emulsion form such as creams, they are fresh, fluid systems, but have the drawbacks of being considered tacky, wetting and very slow-drying.

There is thus still a need to produce cosmetic skincare formulations, especially deodorant and/or antiperspirant products that are stable over time, combining a fresh feeling onto the skin after application, a very fast penetration, an immediate dry, soft, non-wetting and non-tacky feel, and which are effective in the desired application.

Patent EP1584330 describes antiperspirant compositions under the form of oil-in-water emulsions based on wax of melting point superior to 80° C. especially polyethylene waxes which give a fast drying and a reduced stickyness.

Patent EP 1 550 435 discloses deodorant and/or antiperspirant creams that are stable on storage, in the form of an oil-in-water emulsion containing a surfactant consisting of a mixture of alkylpolyglucoside/fatty alcohol combined with a polyurethane polyether, and which may be conditioned in a grille stick or in a tube, but they remain tacky and slow to dry.

Patent application WO 2004/112 739 describes thick antiperspirant creams having viscosities ranging from 80 000 to 120 000 mPa·s (5 rpm). The compositions contain a high level of co-surfactants (glyceryl stearate), which have a tendency to produce a tacky effect after application.

Henkel patent EP 1 239 822 describes antiperspirant creams containing water, water-insoluble particulate polysaccharides, at least one antiperspirant active agent and at least one wax comprising an ester of a $C_{16-60}$ alcohol and of a $C_8$-$C_{36}$ carboxylic acid. They contain a high proportion of particulate starch which may cause the appearance of white marks on clothing.

We know in the application EP2436369 oil-in-water emulsions based on a mixture of waxes comprising a) at least one paraffin wax and/or at least one polyethylene wax, b) at least one monocrystalline wax and c) at least one animal/plant wax containing an ester of a $C_{20}$-$C_{32}$ fatty acide and a $C_{28}$-$C_{34}$ fatty alcohol in the aim of obtaining creams having a ggod stability on storage, producing onto the skin an elastic sensation and good resilience and stickyness. The Candelilla was associated to the waxy components a) and b) do not allow, according to this document, to obtain a sufficiently stable cream.

We know in the application DE19962878 oil-in-water emulsions with esters waxes of $C_{18}$-$C_{60}$ fatty alcohol and $C_8$-$C_{36}$ monocarboxylic acid and watersoluble polysaccharides. In particular, examples 29 and 30 are oil-in-water emulsions with hydrocarbon oils, non-ionic surfactants having a linear and saturated hydrocarbon chain comprising at least 16 carbon atoms (ceteareth-20, glycerylstearate), a $C_{20}$-$C_{40}$ ester wax: Kesterwachs $C_{20}$-$C_{40}$ Alkylstearate and a polysaccharide (hydroxyethylcellulose and methylhydroxypropylcellulose) and a mixture of fatty alcohols stearylic alcohol/béhenylic alcohol. Those emulsions do not permit to produce a fresh feeling and penetrate very slowly.

The Applicant has discovered that this objective may be achieved with novel emulsions forming creams, which are stable over time, simultaneously having good cosmetic properties: soft feel and immediate dry sensation, non-wetting freshness, absence of tackiness and non-greasy feel, and good efficacy in the desired application.

This discovery forms the basis of the invention.

The present invention relates to a composition in the form of an oil-in-water emulsion, comprising, in a cosmetically acceptable medium:

A) a continuous aqueous phase and

B) an oily phase dispersed in the said aqueous phase and comprising at least one hydrocarbon-based oil;

C) at least one mixture consisting of:

(i) at least one nonionic surfactant containing a saturated linear hydrocarbon-based chain comprising at least 16 carbon atoms, the said surfactant being other so than a fatty alcohol, and ii) at least one fatty alcohol in pure form containing at least 16 carbon atoms or a mixture consisting exclusively of fatty alcohols containing at least 16 carbon atoms;

D) at least one wax with a melting point of greater than 45° C. comprising one or more $C_{40}$-$C_{70}$ ester compounds and not comprising any $C_{20}$-$C_{39}$ ester compounds, in an amount from 1 to 10% by weight relative to the total weight of the composition and E) at least one water-soluble polysaccharide; the said composition having a viscosity, measured at 25° C. with a Rheomat RM 180 viscometer at 200 s$^{-1}$ at room temperature with a No. 3 or No. 4 spindle after 10 minutes, ranging from 1500 mPa·s to 12 000 mPa·s and preferably from 2000 mPa·s to 8000 mPa·s.

The present invention also relates to a cosmetic process for treating and/or caring for human keratin materials, characterized in that it consists in applying to the surface of the keratin material a composition as defined previously.

The present invention also relates to a cosmetic process for treating and/or caring for human keratin materials, characterized in that it consists in applying to the surface of the keratin material a composition as defined previously.

The present invention also relates to a cosmetic process for treating human perspiration and/or perspiration-related body odour, which consists in applying to the surface of a human keratin material a composition as defined previously comprising at least one deodourant active agent and/or one antiperspirant active agent.

Other subjects of the invention will emerge later in the description.

The expression "cosmetically acceptable" means compatible with the skin and/or its appendages or mucous membranes, having a pleasant colour, odour and feel and not causing any unacceptable discomfort (stinging, tautness or redness) liable to discourage the consumer from using this composition.

The expression "human keratin materials" means the skin (body, face, area around the eyes), hair, eyelashes, eyebrows, body hair, nails, lips or mucous membranes.

The term "antiperspirant" means any substance which has the effect of reducing the flow of sweat and/or of reducing the sensation of moisture associated with human sweat, and/or of masking human sweat.

The term "deodourant active agent" refers to any substance that is capable of masking, absorbing, improving and/or reducing the unpleasant odour resulting from the decomposition of human sweat by bacteria.

The term "fatty alcohol" means any non-alkoxylated alcohol comprising a linear saturated hydrocarbon-based chain, in particular consisting of a linear alkyl chain, the said chain comprising at least 10 carbon atoms and a hydroxyl function.

The term "hydrocarbon-based chain" means an organic group predominantly consisting of hydrogen atoms and carbon atoms.

The term "pure fatty alcohol comprising at least 16 carbon atoms" means any non-alkoxylated alcohol consisting of more than 95% by weight of the said alcohol, the said alcohol comprising a saturated linear hydrocarbon-based chain, in particular consisting of a linear alkyl chain, said chain comprising at least 16 carbon atoms and a hydroxyl function.

The term "mixture exclusively consisting of fatty alcohols comprising at least 16 carbon atoms" means any mixture comprising at least two non-alkoxylated alcohols comprising a linear saturated hydrocarbon-based chain, in particular consisting of a linear or branched alkyl chain, the said chain comprising at least 16 carbon atoms and a hydroxyl function; the said fatty alcohol mixture containing less than 1% by weight and preferably less than 0.5% by weight of $C_{12}$-$C_{15}$ fatty alcohol relative to the total weight of the fatty alcohol mixture, or even being free of $C_{12}$-$C_{15}$ fatty alcohol.

The term "ester compound" means any organic molecule comprising a linear or branched, saturated or unsaturated hydrocarbon-based chain comprising at least one ester function of formula —COOR in which R represents a hydrocarbon-based radical, in particular a saturated linear alkyl radical.

The term "wax not comprising any $C_{20}$-$C_{39}$ ester compounds" means any wax containing less than 1% by weight and preferably less than 0.5% by weight of $C_{20}$-$C_{39}$ ester compounds relative to the weight of the wax, or even being free of $C_{20}$-$C_{39}$ ester compounds.

Melting Point

For the purposes of the invention, the melting point corresponds to the temperature of the most endothermic peak observed in thermal analysis (DSC) as described in the standard ISO 11357-3; 1999. The melting point of the surfactant or of the the wax can be measured using a differential scanning calorimeter (DSC), for example the calorimeter sold under the name MDSC 2920 by TA Instruments.

The measurement protocol is as follows:

A sample of 5 mg of wax placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference between the power absorbed by the empty crucible and the power absorbed by the crucible containing the sample of wax as a function of the temperature is measured. The melting point of the compound is the temperature value corresponding to the top of the peak of the curve representing the variation in the difference in power absorbed as a function of the temperature.

Viscosity

The compositions of the invention have a viscosity measured at 25° C. with a Rheomat RM 180 viscometer at 200 s$^{-1}$ at room temperature with a No. 3 or No. 4 spindle after 10 minutes, of between 1500 mPa·s and 12 000 mPa·s and preferably between 2000 mPa·s and 8000 mPa·s.

The measurement of the viscosity of the product is performed with a Rheomat RM 180 viscometer according to the method CID-012-02.

The measurement of the torque necessary to overcome the resistance of the fluid whose viscosity it is desired to determine is performed using an immersed element (spindle or measuring body) rotating at a constant chosen speed (5 rpm→check the rotation speed).

The measurement is performed with a product to be analysed/goblet/measuring body at 25° C. assembly. The spindle used to take the measurements is the No. 3 or No. 4 spindle depending on the viscosity of the product.

The volume of substance introduced into the goblet of the No. 3 or No. 4 spindle is 25 mL.

The support for the system and the measuring body are placed in the machine for the measurement.

Mixture of Surfactants and of Fatty Alcohol

Nonionic Surfactants

The nonionic surfactants in accordance with the invention contain a saturated linear chain comprising at least 16 carbon atoms.

Among the nonionic surfactants, examples that may be mentioned include:
  alkylpolyglucosides in which the alkyl chain comprises at least 20 carbon atoms;
  ethoxylated fatty alcohols comprising at least 20 carbon atoms;

polyglyceryl fatty esters containing a chain comprising at least 20 carbon atoms;
mixtures thereof.

The alkylpolyglucosides generally correspond to the following structure:

R(O)(G)x in which the radical R is a linear or branched alkyl radical containing at least 20 carbon atoms, G is a saccharide residue and x ranges from 1 to 5, preferably from 1.05 to 2.5 and more preferentially from 1.1 to 2.

The saccharide residue may be chosen from glucose, dextrose, saccharose, fructose, galactose, maltose, maltotriose, lactose, cellobiose, mannose, ribose, dextran, talose, allose, xylose, levoglucan, cellulose and starch. More preferentially, the saccharide residue denotes glucose.

It should also be noted that each unit of the polysaccharide part of the alkylpolyglycoside may be in α or β isomer form, in L or D form, and the configuration of the saccharide residue may be of furanoside or pyranoside type.

It is, of course, possible to use mixtures of alkylpolysaccharides, which may differ from each other in the nature of the borne alkyl unit and/or the nature of the bearing polysaccharide chain.

Among the alkylpolyglucosides that may be used according to the invention, mention may be made of cetearylglucoside, such as that present in the commercial product Montanov 68® from SEPPIC or Tegocare CG90® from Evonik, and arachidylpolyglucoside, such as that present in the commercial product Montanov 202® from the company SEPPIC.

Among the ethoxylated fatty alcohols that may be used according to the invention, mention may be made of Beheneth-10, such as the commercial product Eumulgin BA 10 from Cognis.

Among the polyglyceryl fatty esters, mention may be made of polyglyceryl-6 behenate, such as the commercial product Pelemol 6-G22 from Phoenix Chemical or polyglyceryl-10 behenate/eicosadiate, such as the commercial product Nomcort HK-P from Nisshin Oillio.

Use will be made more particularly of alkylpolyglucosides and preferably $C_{16}$-$C_{18}$ alkylpolyglucosides such as cetearylglucoside, and $C_{20}$-$C_{22}$ alkylpolyglucosides such as arachidylpolyglucoside, and more particularly arachidylpolyglucoside.

Fatty Alcohols

The fatty alcohols in accordance with the invention are chosen from:
a pure fatty alcohol comprising at least 16 carbon atoms;
a mixture consisting exclusively of fatty alcohols containing at least 16 carbon atoms.

Mixtures consisting exclusively of fatty alcohols containing at least 16 atoms will be chosen more particularly.

The pure fatty alcohols in accordance with the invention containing at least 16 carbon atoms preferably comprise from 16 to 26 carbon atoms and more preferentially from 16 to 22 carbon atoms.

Among the pure fatty alcohols in accordance with the invention containing more than 16 carbon atoms, mention may be made of:
cetyl alcohol, such as the commercial products Cetanol from the company Kokyu Alcohol Kogyo Co., Ltd. and Alfol 16 Alcohol® from the company Sasol Germany GmbH (Hamburg),
stearyl alcohol, such as the commercial product Kalcol 80-98® from Kao,
arachidyl alcohol, such as the commercial products Hainol 20SS® from the company Kokyu Alcohol Kogyo Co. Ltd and Nacol 20-95® from the company Sasol Germany GMBH (Hamburg),
behenyl alcohol, such as the commercial products Nacol 22-97® and Nacol 22-98® from the company Sasol Germany GMBH (Hamburg),
and mixtures thereof.

The mixtures of fatty alcohols comprise at least 10% by weight of fatty alcohol comprising at least 16 carbon atoms, preferably from 16 to 26 carbon atoms and more preferentially from 16 to 22 carbon atoms. They contain preferably from 20% to 100% and more preferentially from 30% to 100% by weight relative to the weight of the fatty alcohol mixture.

Among the mixtures of fatty alcohols in accordance with the invention containing at least 16 carbon atoms and at least 50% by weight relative to the weight of the fatty alcohol mixture, mention may be made of
a cetearyl alcohol mixture (mixture of cetyl alcohol and stearyl alcohol), such as the mixture comprising 70% by weight of $C_{18}$ fatty alcohol(s) and 30% by weight of $C_{16}$ fatty alcohol(s), such as the commercial product Nafol 1618 S® (Sasol Germany GmbH Hamburg),
mixtures based on at least one $C_{22}$ fatty alcohol, at least one $C_{20}$ fatty alcohol and at least one $C_{18}$ fatty alcohol,
a mixture of arachidyl alcohol and behenyl alcohol.

Among the mixtures based on at least one $C_{22}$ fatty alcohol, at least one $C_{20}$ fatty alcohol and at least one $C_{18}$ fatty alcohol, mention may be made of:
the mixture comprising 77% by weight of $C_{22}$ fatty alcohol(s), 18% by weight of $C_{20}$ fatty alcohol(s) and 5% by weight of $C_{18}$ fatty alcohol(s), such as the commercial product Nafol 1822 C Alcohol® (Sasol Germany GmbH Hamburg) or the commercial product Lanette 22® (Cognis Corporation Care Chemicals);
the mixture comprising 80% by weight of $C_{22}$ fatty alcohol(s), 10% by weight of $C_{20}$ fatty alcohol(s) and 10% by weight of $C_{18}$ fatty alcohol(s), such as the commercial product Behenyl Alcohol 80® (Kokyu Alcohol Kogyo Co. Ltd);
the mixture comprising 44% by weight of $C_{22}$ fatty alcohol(s), 11% by weight of $C_{20}$ fatty alcohol(s) and 43% by weight of $C_{18}$ fatty alcohol(s), such as the commercial product Nafol 1822 Alcohol® (Sasol Germany GmbH Hamburg);
the mixture comprising 6% by weight of $C_{24}$ fatty alcohol(s), 30% by weight of $C_{22}$ fatty alcohol(s), 58% by weight of $C_{20}$ fatty alcohol(s) and 7% by weight of $C_{18}$ fatty alcohol(s), such as the commercial product Nafol 20-22 EN (Sasol Germany GmbH Hamburg).

Use will be made more particularly of behenyl alcohol, arachidyl alcohol, a cetostearyl alcohol, or mixture thereof.

As mixture of nonionic surfactant and of fatty alcohol in accordance with the invention, mention may be made of:
a mixture of arachidyl alcohol, behenyl alcohol and arachidylglucoside, such as the commercial product Montanov 202® from the company SEPPIC,
a mixture of cetearyl alcohol and cetearylglucoside, such as the commercial product Montanov 68® from the company SEPPIC or such as the combination of Tegocare CG90 with Nafol 1822C.
s Use will be made more particularly of a mixture of arachidyl alcohol and behenyl alcohol/arachidylglucoside, such as the commercial product Montanov 202® from the company SEPPIC.

The fatty alcohol/nonionic surfactant mixture is preferably present in the emulsions in accordance with the invention in active material concentrations ranging from 1% to 10% by weight and more preferentially from 2% to 7% by weight relative to the total weight of the emulsion.

The fatty alcohol/nonionic surfactant mixture preferably contains more than 50% by weight of fatty alcohol(s) and more preferentially more than 70% by weight of fatty alcohol(s) relative to the total weight of the said fatty alcohol/nonionic surfactant mixture.

Waxes

The wax under consideration in the context of the present invention is generally a lipophilic compound that is solid at room temperature (25° C.), with a solid/liquid reversible change of state, having a melting point of greater than or equal to 45° C., possibly ranging up to 200° C. and especially up to 120° C.

The waxes that may be used in the compositions according to the invention are chosen from waxes with a melting point of greater than 45° C. comprising one or more $C_{40}$-$C_{70}$ ester compounds and not comprising any $C_{20}$-$C_{39}$ ester compounds.

The waxes according to the invention may also be used in the form of a mixture of waxes.

The content of ester comprising from 40 to 70 carbon atoms and preferably ranges from 20% to 100% by weight and preferably from 20% to 90% by weight relative to the total weight of wax(es).

Use will be made more particularly of candelilla wax and/or beeswax.

The composition according to the invention may comprise a wax content preferably ranging from 1% to 10% by weight and in particular from 2% to 8% by weight relative to the total weight of the composition.

Water-Soluble Polysaccharides

The term "polysaccharide" means any polymer consisting of several saccharides (or monosaccharides) having the general formula:

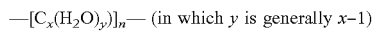

—$[C_x(H_2O)_y)]_n$— (in which $y$ is generally $x$−1)

and linked together via O-oside bonds.

The water-soluble polysaccharides that may be used in the present invention are especially chosen from starches, gellans, scleroglucan gum, guar gum, konjac, agar, and celluloses such as hydroxyethylcellulose and hydroxypropylcellulose, and mixtures thereof.

Starches are preferably used.

The "term water-soluble" means partially or totally soluble in water to give a gelled or thickened solution at a concentration of 1% active material in water, after implementation with or without heating.

The starches that may be used in the present invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the botanical origin of the starches. The amylose/amylopectin weight ratio may range from 30/70 (corn) to 16/84 (rice). The molecular weight of the amylose is preferably up to 1 million by weight and that of the amylopectin is preferably from 100 to 500 million by weight.

The starch molecules used in the present invention may be unmodified or chemically or physically modified.

Their botanical origin may be cereals or tubers. Thus, the natural starches may be chosen from corn starch, rice starch, tapioca starch, cassava starch, barley starch, potato starch, wheat starch, sorghum starch, palm starch and pea starch.

Among the unmodified starches, mention may be made of unmodified corn starches (INCI name: *Zea mays* starch), for instance the products sold under the trade name Farmal CS®, in particular the commercial product Farmal CS 3650® from the company Corn Products International.

Mention may also be made of unmodified rice starches (INCI name: *Oryza sativa* (rice) starch), for instance the commercial product Remy DR I® sold by the company Beneo-Remy.

According to a particular form of the invention, starches used are modified by crosslinking with functional agents capable of reacting with the hydroxyl groups of the starch molecules, which will thus bond together (for example with glyceryl and/or phosphate groups).

Monostarch phosphates (of the type St-O—PO—(OX)$_2$), distarch phosphates (of the type St-O—PO—(OX)—O-St) or even tristarch phosphates (of the type St-O—PO—(O-St)$_2$) or mixtures thereof may especially be obtained by crosslinking with phosphorus compounds.

X especially denotes alkali metals (for example sodium or potassium), alkaline-earth metals (for example calcium or magnesium), ammonium salts, amine salts, so for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Use will preferentially be made of distarch phosphates or of compounds rich in distarch phosphate, in particular the distarch phosphate hydroxypropyl ethers having the INCI name: Hydroxypropyl Starch Phosphate, for instance the products sold under the trade names Farinex VA70 C or Farmal MS 689® from the company Avebe Stadex; the products sold under the trade names Structure BTC®, Structure HVS®, Structure XL® or Structure Zea® from National Starch (corn distarch phosphate).

Preferentially, the starch will be chosen from unmodified corn starches, unmodified rice starches and corn distarch phosphates, or mixtures thereof.

Even more preferentially, starch will be chosen from corn distarch phosphates.

According to the invention, the water-soluble polysaccharide(s) may preferably represent from 0.5% to 6% by weight and more particularly from 1% to 4% by weight relative to the total weight of the final composition.

Aqueous Phase

The term "aqueous phase" means a phase comprising water and generally any molecule in dissolved form in water in the composition.

The aqueous phase of the said compositions comprises water and generally other water-soluble or water-miscible solvents. The water-soluble or water-miscible solvents comprise monoalcohols with a short chain, for example of $C_1$-$C_4$, such as ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol, glycerol and 1,3-propanediol will be used more particularly.

The concentration of the aqueous phase preferably ranges from 50% to 90% by weight and preferably from 60% to 90% by weight relative to the total weight of the composition.

Oily Phase

The compositions according to the invention contain at least one water-immiscible organic liquid phase, known as an oily phase. This phase generally comprises one or more hydrophobic compounds that make said phase water-immiscible. The said phase is liquid (in the absence of structuring agent) at room temperature (20-25° C.).

Preferentially, the water-immiscible organic-liquid organic phase in accordance with the invention generally comprises at least one volatile or non-volatile hydrocarbon-based oil and optionally at least one volatile or non-volatile silicone oil.

The term "oil" means a fatty substance that is liquid at room temperature (25° C.) and atmospheric pressure (760 mmHg, i.e. $10^5$ Pa). The oil may be volatile or non-volatile.

For the purpose of the invention, the term "volatile oil" means an oil that is capable of evaporating on contact with the skin or the keratin fibre in less than one hour, at room temperature and atmospheric pressure. The volatile oils of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The oils in accordance with the invention are preferably chosen from any cosmetically acceptable oil, especially mineral, animal, plant or synthetic oils, especially hydrocarbon-based oils or silicone oils, or mixtures thereof.

The term "hydrocarbon-based oil" means an oil mainly containing carbon and hydrogen atoms and possibly one or more functions chosen from hydroxyl, ester, ether and carboxylic functions. Generally, the oil has a viscosity of from 0.5 to 100 000 mPa·s and preferably from 50 to 50 000 mPa·s and more preferably from 100 to 30 000 mPa·s.

The term "silicone oil" means an oil comprising in its structure carbon atoms and at least one silicon atom.

As examples of volatile hydrocarbon-based oils that may be used in the invention, mention may be made of:
volatile hydrocarbon-based oils chosen from hydrocarbon-based oils containing from 8 to 16 carbon atoms, and in particular $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in patent application DE 10 2008 012 457 from Cognis.

As examples of non-volatile hydrocarbon-based oils that may be used in the invention, mention may be made of:
hydrocarbon-based plant oils, such as liquid triglycerides of fatty acids of 4 to 24 carbon atoms, such as heptanoic or octanoic acid triglycerides, or else wheatgerm oil, olive oil, sweet almond oil, palm oil, rapeseed oil, cottonseed oil, alfalfa oil, poppy seed oil, pumpkin seed oil, marrow oil, blackcurrant oil, evening primrose oil, millet oil, barley oil, quinoa oil, rye oil, safflower oil, candlenut oil, passionflower oil, musk rose oil, sunflower oil, corn oil, soybean oil, marrow oil, grape seed oil, sesame oil, hazelnut oil, apricot oil, macadamia oil, castor oil, avocado oil, caprylic/capric acid triglycerides, such as those sold by Stearineries Dubois or those sold under the names Miglyol 810, 812 and 818 by Dynamit Nobel, jojoba oil or shea butter oil;

synthetic ethers containing from 10 to 40 carbon atoms, such as dimethyl ether;

synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$-$C_{15}$ alkyl benzoates, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetra isostearate;

linear or branched hydrocarbons, of mineral or synthetic origin, such as liquid paraffins and derivatives thereof, petroleum jelly, polydecenes, polybutenes, hydrogenated polyisobutene such as Parleam, and squalane, fatty alcohols which are liquid at room temperature and which comprise a branched and/or unsaturated carbon-based chain containing from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates;

acetates;

citrates.

Among the volatile silicones, mention may be made of volatile linear or cyclic silicone oils, especially those with a viscosity 8 centistokes ($8 \times 10^{-6}$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of the volatile linear alkyltrisiloxane oils of general so formula (I):

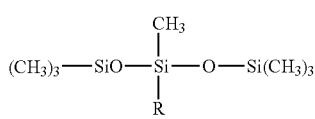

in which R represents an alkyl group containing from 2 to 4 carbon atoms, of which one or more hydrogen atoms may be substituted with a fluorine or chlorine atom.

As examples of non-volatile silicone oils, mention may be made of linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof. Use will be made more particularly of a linear non-volatile polydimethylsiloxane (PDMS).

Preferably, the oily phase comprises at least one non-volatile hydrocarbon-based oil and optionally at least one non-volatile silicone oil.

The hydrocarbon-based oil will preferably be chosen from triglycerides such as caprylic/capric acid triglycerides, fatty acid esters such as isopropyl palmitate, ethers such as dimethyl ether, alkanes such as isohexadecane, and mixtures thereof.

The hydrocarbon-based oil(s) will preferably be present in the composition in concentrations ranging from 5% to 30% by weight and more preferentially ranging from 5% to 20% by weight relative to the total weight of the composition.

The concentration of the oily phase preferably ranges from 10% to 30% relative to the total weight of the composition.

Associate Nonionic Polymer

According to a particularly preferred form, the compositions also comprise at least one nonionic associative polymer.

For the purposes of the present invention, the term "associative polymers" means hydrophilic polymers that are capable, in an aqueous medium, of reversibly associating with each other or with other molecules. Their chemical structure more particularly comprises at least one hydrophilic region and at least one hydrophobic region.

The term "hydrophobic group" is understood to mean a radical or polymer comprising a saturated or unsaturated and linear or branched hydrocarbon-based chain. When the hydrophobic group denotes a hydrocarbon-based radical, it comprises at least 10 carbon atoms, preferably from 10 to 30 carbon atoms, in particular from 12 to 30 carbon atoms and more preferentially from 18 to 30 carbon atoms. Preferentially, the hydrocarbon-based group is derived from a monofunctional compound.

By way of example, the hydrophobic group may be derived from a fatty alcohol, such as stearyl alcohol, dodecyl alcohol or decyl alcohol, or else from a polyoxyalkylenated fatty alcohol, such as Steareth-100. It may also denote a hydrocarbon-based polymer, for instance polybutadiene.

The nonionic associative polymers may be chosen from:
cellulases modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS ($C_{16}$ alkyls) sold by the company Aqualon, celluloses modified with alkylphenyl polyalkylene glycol ether groups, such as the product Amercell Polymer HM-1500 (nonylphenyl polyethylene glycol (15) ether) sold by the company Amerchol, guars such as hydroxypropyl guar, modified with groups comprising at least one fatty chain such as an alkyl chain, inulins modified with groups comprising at least one fatty chain, such as alkyl carbamate inulins and in particular the lauryl carbamate inulin sold by the company Orafti under the name Inutec SP1, diesters of polyethylene glycol and of a fatty acid, such as polyethylene glycol (150 OE) distearate, for instance PEG-150 distearate sold under the trade name Emcol L 32-45® by Witco.

The concentration of the diester(s) of polyethylene glycol and of a fatty acid may range for example from 0.1% to 10% by weight, preferably from 0.25% to 6% by weight and better still from 0.5% to 3% by weight relative to the total weight of the composition, associative polyurethanes.

Associative polyurethanes are nonionic block copolymers comprising in the chain both hydrophilic blocks usually of polyoxyethylene nature (polyurethanes may also be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be provided. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to a preferred embodiment, a nonionic associative polymer of polyurethane type is used as gelling agent.

As examples of nonionic fatty-chain polyurethane polyethers that may be used in the invention, it is also possible to use Rheolate® FX 1100 (Steareth-100/PEG 136/HDI (hexamethyl diisocyanate) copolymer), Rheolate® 205® containing a urea function, sold by the company Elementis, or Rheolate® 208, 204 or 212, and also Acrysol RM 184® or Acrysol RM 2020.

Mention may also be made of the product Elfacos T210® containing a C12-C14 alkyl chain, and the product Elfacos T212® containing a C16-18 alkyl chain (PPG-14 Palmeth-60 Hexyl Dicarbamate) from Akzo.

The product DW 1206B® from Röhm & Haas containing a C20 alkyl chain and a urethane bond, sold at a solids content of 20% in water, may also be used.

Use may also be made of solutions or dispersions of these polymers, especially in water or in aqueous-alcoholic medium. Examples of such polymers that may be mentioned are Rheolate® 255, Rheolate® 278 and Rheolate® 244 sold by the company Elementis. Use may also be made of the products DW 1206F and DW 1206J sold by the company Röhm & Haas.

The associative polyurethanes that may be used according to the invention are in particular those described in the article by G. Fonnum, J. Bakke and Fk. Hansen—Colloid Polym. Sci., 271, 380-389 (1993).

Even more particularly, according to the invention, use may also be made of a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Röhm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Use may also be made of solutions or dispersions of these polymers, especially in water or in aqueous-alcoholic medium. Examples of such polymers that may be mentioned include Rheolate FX1010®, Rheolate FX1035® and Rheolate 1070® from the company Elementis, and Rheolate 255®, Rheolate 278® and Rheolate 244® sold by the company Elementis. Use may also be made of the products Aculyn 44, Aculyn 46®, DW 1206F® and DW 1206J®, and also Acrysol RM 184 from the company Röhm & Haas, or alternatively Borchigel LW 44® from the company Borchers, and mixtures thereof.

Use will be made more particularly of an associative nonionic polyurethane polyether such as the product sold especially by the company Elementis under the name Rheolate FX 1100®, which is a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight of 30 000 (INCI name: PEG-136/Steareth-100I/SMDI Copolymer).

The amount of associative nonionic polymer(s) as active material may range, for example, from 0.1% to 10% by weight, preferably from 0.25% to 6% by weight and better still from 0.5% to 3% by weight relative to the total weight of the composition.

Additives

The compositions according to the invention may also furthermore comprise additional cosmetic and dermatological active agents.

The cosmetic compositions according to the invention may comprise cosmetic adjuvants chosen from opacifiers, stabilizers, preserving agents, polymers, fragrances, thickeners, sunscreens, dermatological or cosmetic active agents, fillers, suspension agents, dyestuffs or any other ingredient usually used in cosmetics for this type of application.

Among the fillers, mention may be made of talc, kaolin, silicas, clays, perlite and water-insoluble particulate starches.

Among the silicas, mention may be made of:
porous silica microspheres, especially porous silica microspheres. The porous spherical silica microparticles preferably have a mean particle size ranging from 0.5 to 20 µm and more particularly from 3 to 15 µm. They preferably have a specific surface area ranging from 50 to 1000 $m^2/g$ and more particularly from 150 to 800 $m^2/g$. They preferably have a specific pore volume ranging from 0.5 to 5 ml/g and more particularly from 1 to 2 ml/g. As examples of porous silica microbeads, use may be made of the following commercial products: Silica Beads SB 150® from Miyoshi Sunsphere H-51®; Sunsphere H53® and Sunsphere H33® from Asahi Glass MSS-500-3H® from the company Kobo Sunsil 130® from Sunjin Spherica P-1500® from Ikeda Corporation Sylosphere® from Fuji Silysia;

polydimethylsiloxane-coated amorphous silica microspheres, especially those sold under the name SA Sunsphere® H33, amorphous hollow silica particles, especially those sold under the name Silica so Shells by the company Kobo, precipitated silica powders surface-treated with a mineral wax, such as the precipitated silica treated with a polyethylene wax and especially those sold under the name Acematt OR 412 by the company Evonik-Degussa.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

The dermatological or cosmetic active agents may be chosen especially from moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-seborrhoeic agents, astringents, cicatrizing agents, anti-inflammatory agents, keratolytic agents, agents for preventing hair regrowth and antiacne agents.

Deodourant and/or Antiperspirant Compositions

The present invention also relates to a cosmetic process for treating human perspiration and/or perspiration-related body odour, which consists in applying to the surface of a human keratin material a composition as defined previously comprising at least one deodourant active agent and/or one antiperspirant active agent.

The compositions in accordance with the invention may thus be used as deodourants and/or antiperspirants and may contain at least one deodourant active agent and/or one antiperspirant active agent.

Additional Antiperspirant Salts or Complexes

The aluminium and/or zirconium antiperspirant salts or complexes are preferably chosen from aluminium halohydrates; aluminium zirconium halohydrates, complexes of zirconium hydroxychloride and of aluminium hydroxychloride with or without an amino acid, such as those described in U.S. Pat. No. 3,792,068.

Among the aluminium salts, mention may be made in particular of aluminium chlorohydrate in activated or unactivated form, aluminium chlorohydrex, the aluminium chlorohydrex-polyethylene glycol complex, the aluminium chlorohydrex-propylene glycol complex, aluminium dichlorohydrate, the aluminium dichlorohydrex-polyethylene glycol complex, the aluminium dichlorohydrex-propylene glycol complex, aluminium sesquichlorohydrate, the aluminium so sesquichlorohydrex-polyethylene glycol complex, the aluminium sesquichlorohydrex-propylene glycol complex, aluminium sulfate buffered with sodium aluminium lactate.

Among the aluminium-zirconium salts, mention may be made in particular of aluminium zirconium octachlorohydrate, aluminium zirconium pentachlorohydrate, aluminium zirconium tetrachlorohydrate and aluminium zirconium trichlorohydrate.

The complexes of zirconium hydroxychloride and of aluminium hydroxychloride with an amino acid are generally known as ZAG (when the amino acid is glycine). Among these products, mention may be made of the aluminium zirconium octachlorohydrex-glycine complexes, the aluminium zirconium pentachlorohydrex-glycine complexes, the aluminium zirconium tetrachlorohydrex-glycine complexes and the aluminium zirconium trichlorohydrex-glycine complexes.

The aluminium and/or zirconium antiperspirant salts or complexes may be present in the composition according to the invention in a proportion of at least 0.5% by weight and preferably from 0.5% to 25% by weight relative to the total weight of the composition.

Deodorant Active Agents

The compositions according to the invention may also furthermore contain one or more additional deodorant active agents.

The term "deodorant active agent" refers to any substance that is capable of masking, absorbing, improving and/or reducing the unpleasant odour resulting from the decomposition of human sweat by bacteria.

The deodorant agents may be bacteriostatic agents or bactericides that act on underarm odour microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the company Symrise), glycerol derivatives, for instance caprylic/capric glycerides (Capmul MOM from Abitec), glyceryl caprylate or caprate (Dermosoft GMCY and Dermosoft GMC, respectively from Straetmans), polyglyceryl-2 caprate (Dermosoft DGMC from Straetmans), and biguanide derivatives, for instance polyhexamethylene biguanide salts; chlorhexidine and salts thereof; 4-phenyl-4,4-dimethyl-2-butanol (Symdeo MPP from Symrise); cyclodextrins.

Among the deodorant active agents in accordance with the invention, mention may also be made of
zinc salts, for instance zinc salicylate, zinc gluconate, zinc pidolate; zinc sulfate, zinc chloride, zinc lactate, zinc phenolsulfonate; zinc ricinoleate;
sodium bicarbonate;
salicylic acid and derivatives thereof such as 5-n-octanoylsalicylic acid;
zeolites, especially silver-free metallic zeolites;
alum;
triethyl citrate.

The deodorant active agents may preferably be present in the compositions according to the invention in weight concentrations ranging from 0.01% to 10% by weight relative to the total weight of the composition.

The examples that follow serve to illustrate the present invention. The amounts are given as mass percentages relative to the total weight of the composition.

Galenical Forms

The compositions according to the invention are in the form of a soft solid stick whose consistency may vary as a function of the desired application, the region of human keratin material to be treated and the desired conditioning, such as a cosmetic product for caring for, holding or colouring the skin or the hair, or a body hygiene product, especially such as a deodourant and/or antiperspirant.

Conditioning

The compositions of the invention may especially be conditioned in a tube, in a device equipped with a perforated wall, especially a grille. In this regard, they comprise the ingredients generally used in products of this type, which are well known to a person skilled in the art.

The present invention consists in particular of a dispensing device, characterized in that it comprises:
a container (12) comprising a deformable wall,
a composition as defined previously, stored in the container, and
a dispensing head (16) closing off the container (12) and comprising an application wall (30) defining at least one product dispensing orifice (82A, 82B).

To extract the product from the container, a pressure is exerted on the container, in order to push the product out of the container via the dispensing orifice. The product is then collected before being applied to the keratin surface.

A dispensing device that is particularly suited to this composition will be described with reference to the attached drawings, in which.

Throughout the following text, the terms "upstream" and "downstream" are understood generally to mean with respect to the normal direction of circulation of a fluid, in particular a cosmetic product.

The device 310 is intended to store, dispense and apply the cosmetic composition onto a keratin surface, especially the skin, of a user.

Figures 1, 2:
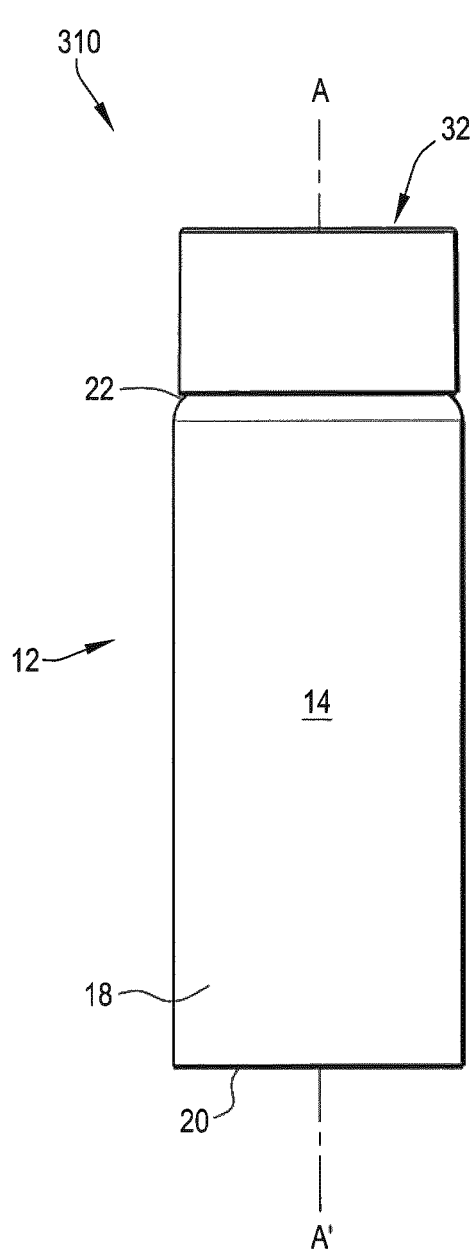
FIG. 1 is a side view of a dispensing device, the lid occupying its closing-off position.
FIG. 2 is a perspective view of three-quarters of the face of the device of FIG. 1, the lid having been removed from the dispensing head.

The dispensing device 310 comprises a container 12 delimiting an inner volume 14 for receiving the cosmetic product, and a head 16 for dispensing cosmetic product, closing off the container 12 (visible in FIG. 2).

In the example shown in FIGS. 1 and 2, the container 12 comprises a wall 18 which advantageously forms a tube. The wall 18 is closed off in a leaktight manner at its upstream end 20 opposite the head 16. At its downstream end 22, the wall 18 is closed off by the head 16.

The base of the wall 18 is advantageously closed by pinching and by soldering the wall 18.

The wall 18 is deformable. The term "deformable" means that the wall can be deformed when pressed by the user, for example when it is squeezed between a user's fingers.

The wall may be sufficiently rigid to return to its initial position when the exerted pressure is released, for example when the wall is made of a mixture of polyethylene (PE) comprising 30% low-density polyethylene (LDPE) and 70% high-density polyethylene (HDPE). The advantage of having a sufficiently rigid wall is that it affords the user good handling of the device to facilitate the application of the product.

As a variant, it is possible for the wall not to return to its initial position when the pressure is released; in this case, the wall remains in its deformed position, for example when the wall is made mainly of low-density polyethylene (LDPE) or of a metallic material.

The container 12 extends along a longitudinal general axis A-A' between the ends 20, 22.

Advantageously, the head 14 is engaged on the neck of the container 12 and is attached to the neck by click-fastening. To this end, the head 14 is click-fastened onto the neck of the container 12 and is held on the neck by stops.

As a variant, the head 16 is attached by soldering, or by overmoulding of the wall 18 of the container 12 onto the head 14. In another variant, the head 14 and the container 12 are at least partially made from the same material.

The inner volume 14 is delimited inside the container 12. It contains the cosmetic composition.

When the user wishes to apply the cosmetic product, he extracts the cosmetic product present in the inner volume 14 by generating a pressure of product in the inner volume 14, for example by exerting a pressure on the deformable wall of the container 12.

As a variant, not shown, the container is a tube comprising an inner deformable pocket making it possible to delimit a volume containing the cosmetic composition and a volume not containing any composition in the container. The deformable wall of the tube is closed off at its upstream end onto the dispensing head and is closed at its downstream end. The wall of the tube may have an air intake orifice in communication with the inner volume of the container not containing any composition. The deformable wall of the tube is sufficiently rigid to return to its initial position when the exerted pressure is released, whereas it is possible for the pocket, for its part, not to return to its initial position. The volume containing the composition is in communication with the dispensing head. Thus, to dispense the composition, the user exerts a pressure on the tube while holding, for example, a finger over the air intake orifice to close it off. The excess air pressure generated in the tube, especially in the volume of the container not containing any composition, is then exerted on the pocket and on the volume of the container containing the composition so as to expel the product via the dispensing head.

Figure 3:
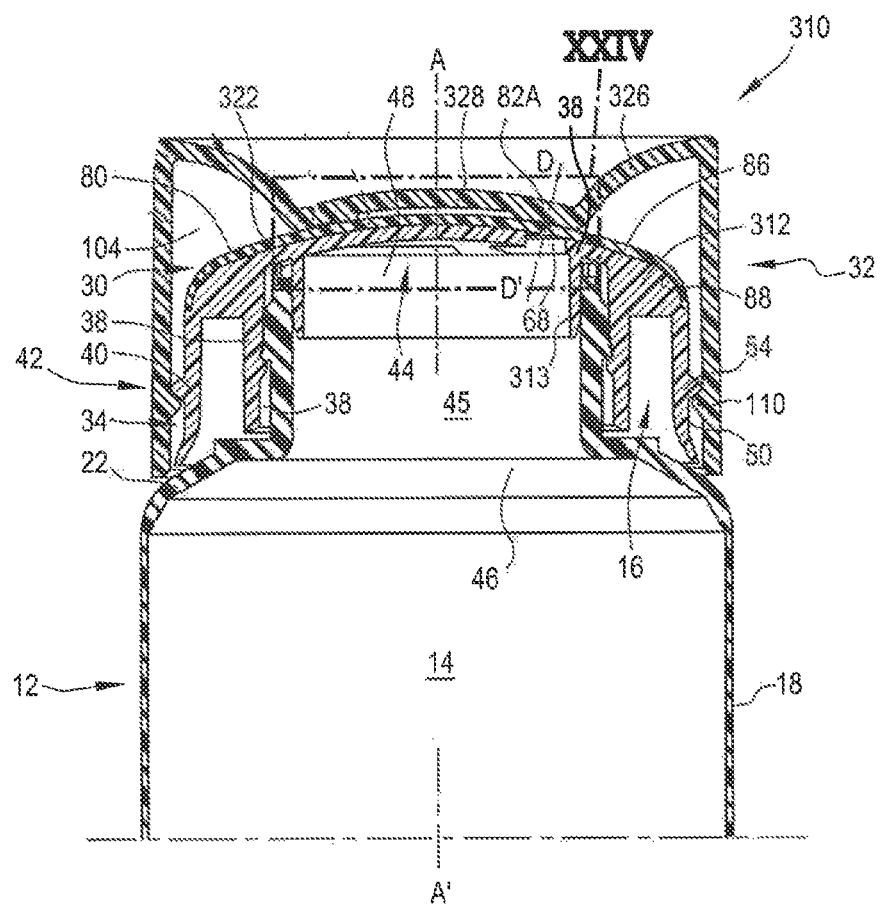
FIG. 3 is a view in cross section along a vertical median plane of the device of FIG. 1.
Figure 11:
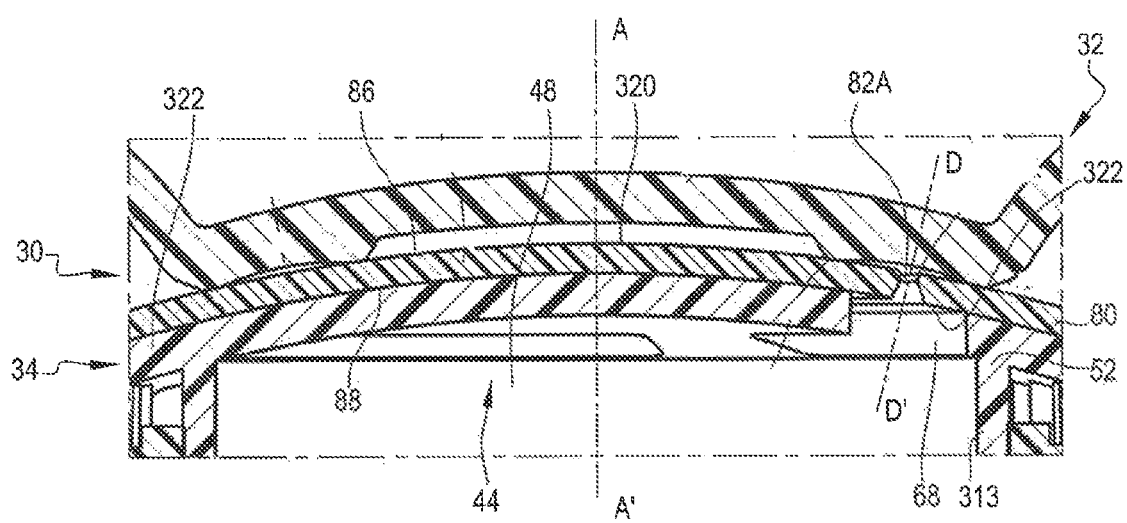
FIG. 11 is a view of a detail labelled XXIV in FIG. 3.

As illustrated in FIGS. 2, 3 and 11, the head 14 comprises an application wall 30 and optionally a lid 32 intended to crown the application wall 30. It advantageously comprises a support 34 bearing the application wall 30.

As illustrated in FIG. 3, the support 34 comprises an inner skirt 38 connected to the wall 18 of the container 12, and an outer sleeve 40 for attaching the lid 32 fitted around the skirt 38. The support 34 also comprises at least one member 42 for retaining the lid 32 on the support 34 and, with reference to FIG. 6, a perforated reinforcement 44 for holding the application wall 30.

In this example, the support 34 is made as a single piece, being made from the same material. It is made, for example, by injection moulding using a thermoplastic material that is more rigid than that forming the application wall 30, such as polyethylene (PE), polypropylene (PP), or mixtures thereof. As a variant, the support 34 directly forms the application wall 30.

The skirt 38 delimits a central product circulation passage 45 which emerges via an upstream aperture 46 via a downstream aperture 48. The circulation passage 45 extends downstream the inner volume 14.

The sleeve 40 comprises a peripheral tubular wall 50 and a downstream bridge 312 connecting it to the skirt 38. The skirt 38 advantageously delimits an annular rim 52 which partially projects towards the axis A-A', the rim 52 being extended upstream by a sealing skirt 313 inserted in the neck of the container 12 to retain the product.

In this example, the support 34 has a cross section of circular outer contour. As a variant, the outer contour is elongated, for example oval or polygonal.

In the example shown in the figures, the lid 32 can be screwed onto the support 34. The retaining member 42 is then formed by a thread 54 projecting radially outwards relative to the sleeve 40. As a variant, the lid 32 is click-fastened onto the support 34. When it is present, the retaining member 42 is formed, for example, by click-fastening or holding means by gripping the lid 32.

The reinforcement 44 projects transversely into the passage 45 at the downstream aperture 48. It is rigid or semi-rigid.

The reinforcement 44 is perforated. In the example illustrated in FIG. 6, the reinforcement 44 comprises an inner disk 62 and a plurality of outer lugs 64 for connecting between the rim 52 of the skirt 38 and the reinforcement 44.

The outer lugs 64 connect the rim 52 of the skirt 38 to the disk 62. They define, between the skirt 38 and the disk 62, a plurality of outer apertures 68 for the passage of product.

In this example, the outer lugs 64 define several C-shaped apertures 68 opening towards each other facing the axis A-A'.

In this example, the number of apertures 68 is equal to 3. More generally, this number is between 1 and 10.

The inner disk 62 has an outer contour contained in the inner contour of the skirt 38.

The application wall 30 is advantageously formed by a body 80 made of polymeric material. The thickness of the body 80 is, for example, less than 5 mm. The body 80 is advantageously made from an elastomer, such as elastomer, thermoplastic or thermoplastic elastomer material, PEBD, PVC, PU, thermoplastic elastomer polyesters, especially copolymers of butylene terephthalate and of esterified polytetramethylene glycol oxide, Hytrel®, EPDM, PDM, EVA, SIS, SEBS, SBS, latex, silicone, nitrile, butyl, polyurethane, polyether block amide, polyester or a copolymer of ethylene and of α-olefin.

The support 34 and the wall 30 are advantageously formed by twin injection of material. In one variant, the support 34 and the wall 30 are formed by injection of the same material.

In this example, the body 80 has an outer contour whose shape is substantially complementary to the outer contour of the support 34. It is thus capable of covering the support 34 to close off the downstream aperture 48.

In this example, the body 80 has a convex dome shape, of convexity directed downstream. It bears at its periphery on the support and is attached thereto. To this end, it is applied to the annular rim 52 and to the bridge 312.

In addition, the body 80 rests on the perforated reinforcement 44, being attached thereto.

The convex dome advantageously has a circular contour, for example with a diameter of greater than 20 mm, better still greater than 30 mm, for example equal to 35 mm. The radius of curvature of the convex dome is, for example, between 30 mm and 150 mm.

Figure 4:
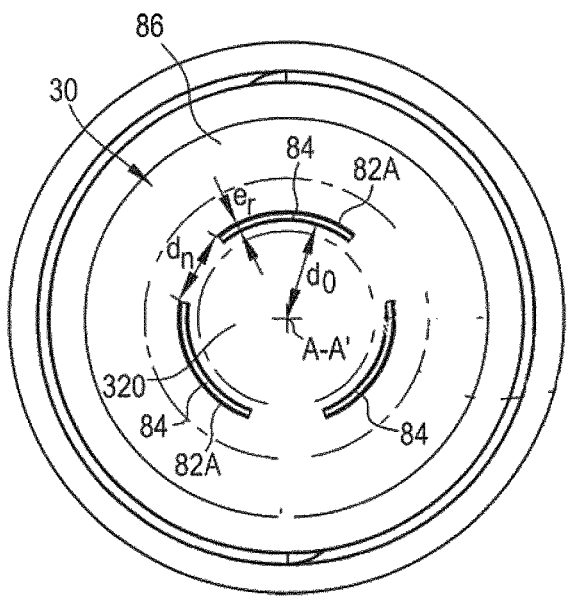
FIG. 4 is a top view of the dispensing head of the device of FIG. 1.
Figure 5:
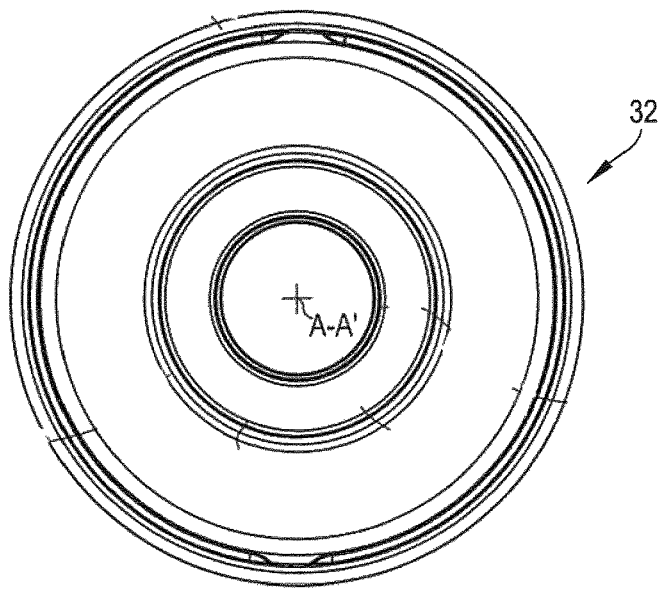
FIG. 5 is a bottom view of the lid for closing off the device of FIG. 1.
Figure 6:
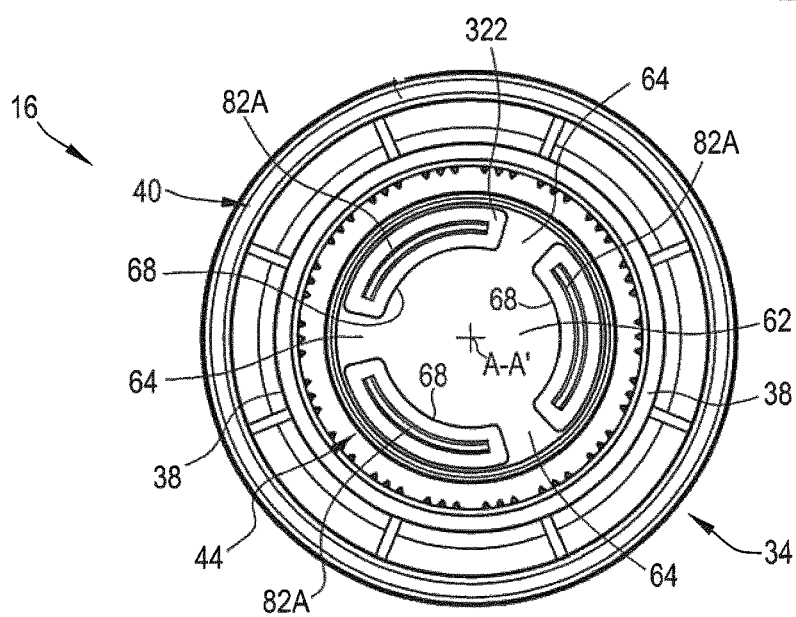
FIG. 6 is a bottom view of the head of the device of FIG. 1.

As illustrated by FIGS. 4 and 6, the body 80 of the wall 30 delimits at least one product dispensing orifice 82A, passing through the body 80 to emerge facing the downstream aperture 48, advantageously facing the passage apertures 68 made in the reinforcement 44.

In the example represented in the figures, the body 80 of the application wall 30 delimits a plurality of dispensing orifices 82A, which are especially C-shaped.

The orifices 82A advantageously extend facing the apertures 68.

In this example, the dispensing orifices 82A are formed by incurved slits 84 made through the body 80 between a downstream surface 86 of the body 80 and an upstream surface 88 of the body 80. The downstream surface 86 forms the application surface of the convex dome.

In this example, the slits 84 extend, in section in a median plane, along a general axis D-D' corresponding to a normal N to the downstream surface 86, taken at the outlet of the slit 84. As a variant, the slits 84 extend along an axis D-D' which is inclined relative to a normal N to the downstream surface 86.

As illustrated in FIG. 4, the dispensing orifices 82A are eccentric relative to the central axis A-A' of the wall 30. The central axis A-A' is defined as the axis passing through the centre of the downstream surface 86 of the wall 30, normal to this surface. In this example, the central axis A-A' is the same as the general axis A-A' of container 12.

Figure 7:
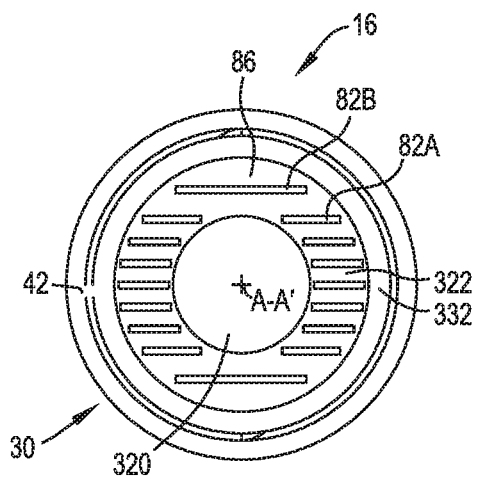
FIGS. 7 to 10 are views similar to FIG. 4 of dispensing head variants.

The distance do radially separating the axis A-A' of each orifice 82A is greater than the maximum radial extent er of each orifice 82A. Thus, as illustrated by FIG. 7, the wall 30 has a solid central zone 320, lacking an orifice 82A, in particular at the axis A-A'.

The slits 84 have a length which is very much greater than their radial extent er. Thus, the length of each slit 84 is at least greater than twice the maximum radial extent er of the slit 84. It should be noted that the radial extent er is then the smallest transverse dimension measured between two opposite edges of the dispensing orifice.

More generally, the maximum radial extent er of each orifice 82A, taken relative to the axis A-A', is less than 1.3 mm and especially less than 1 mm. This transverse extent is advantageously between 0.4 mm and 0.8 mm and better still between 0.5 mm and 0.7 mm, for example equal to 0.6 mm; in this case, the edges of each orifice 82A are permanently located separated from each other.

The length of the slits 84 may be greater than 2.5 mm, for example equal to 10 mm.

Furthermore, for each slit with a radial extent er of less than 1.3 mm, the coefficient determined by the ratio of the area of the orifice to the perimeter of the said orifice may advantageously be less than 0.6, or even less than 0.4 and better still less than 0.3. The smaller this coefficient, the greater the length of the slit and the smaller its area. A large perimeter thus makes it possible to dispense product over a large extent of the application surface, whereas a small area makes it possible to limit and to control the amount of product dispensed.

The orifices 82A are disjointed, i.e. they are separated from each other by solid regions of the application wall 30. In this example, the minimum distance do separating two adjacent orifices 82A is greater than the maximum radial extent er of each orifice 82A.

In the example of FIG. 4, the orifices 82A are angularly distributed around the axis A-A' along a circumference around this axis.

The angular extent of each orifice 82A taken around the axis A-A' is less than 360°/N in which N is the number of orifices 82A on a circumference. The angular extent of each orifice 82A is especially less than (360°-10N)/N.

Each dispensing orifice 82A is placed facing an aperture 68.

However, each orifice 82A has an area less than the area of the aperture 68 opposite which it is placed. Thus, as illustrated in FIG. 6, the wall 30 defines about each orifice 82A, and facing the aperture 68, a peripheral rim 322.

As a variant, each orifice 82A has an extent substantially equal to the aperture 68 opposite which it is placed. In yet another variant, the orifice 82A is located along an edge of the aperture 68, being off-centred relative to the aperture 68. In this case, the peripheral rim 322 has a substantial width and is capable of directing the dispensing of product through the orifice 82A to improve its distribution over the downstream surface 86.

In the example represented in FIGS. 1 to 6, the downstream surface 86 of the wall is smooth. To this end, it is free of macroscopic roughness or unevenness.

The term "macroscopic roughness or unevenness" means roughness or unevenness with a thickness, taken perpendicular to a normal to the wall 30, greater than the thickness of the wall 30.

Thus, the wall 30 is capable of gliding over a user's skin. It is especially free of macroscopic roughness or unevenness at the periphery of the apertures 82A, which allows pleasant application of product over an area of the user's body.

In the dispensing position, a lid 32 is provided separated from the support 34 and from the application wall 30.

In this position, and as will be seen hereinbelow, the dispensing orifices 82A are freed to allow the passage of cosmetic product from the inner volume 14 through the passage 45 to the downstream surface 86 of the application wall.

In the example in which the lid 32 is intended to be screwed onto the support 34, the additional retaining member 110 is formed by a thread additional to the thread present on the support 34.

The application wall 30 is advantageously manufactured as a single piece by moulding.

The orifices 82A, 82B are then manufactured, either during the moulding of the application wall 30, or subsequent to this moulding, by making apertures via laser or mechanical cutting of the wall 30.

The use of a flexible material to make the application wall 30 ensures that the moulding of the orifices 82A, 82B can be performed simply.

The device 310 according to the invention functions as follows.

Initially, when the device 310 is stored, the lid 32 occupies its closing-off position engaged on the support 34, as shown in FIG. 1. The application wall 30 is received in an upstream volume 104. The retaining members 54, 110 co-operate together to hold the lid 32 in position relative to the support 34 and relative to the application wall 30.

When the user wishes to apply cosmetic product, he removes the lid 32 to separate it from the head 16. Next, he extracts the cosmetic product present in the inner volume 14 by generating a pressure of product in the inner volume 14.

The cosmetic product present in the container 12 then passes into the passage 45. It then flows through the orifices 82A to the downstream surface 86 of the application wall 30. The cosmetic product can raise the rim 322 around the orifice 82A.

The cosmetic product then becomes deposited on the downstream surface 86.

The user brings the downstream surface 86 of the application wall 30 in contact with a body surface, for example in contact with the skin. The cosmetic product then becomes deposited on the body surface.

When the user has finished applying product, he returns the lid 32 to its closing-off position.

In one variant, the downstream surface 86 of the application wall is textured. It has, for example, a plurality of hollows and bumps, like on a golf ball.

In one variant, illustrated, for example, by FIG. 7, the dispensing orifices 82A, 82B are rectilinear, and not incurved.

The orifices 82A, 82B have lengths that may be different from each other. For example, a first group of orifices 82A has a length shorter than that of a second group of orifices 82B.

Figure 8:
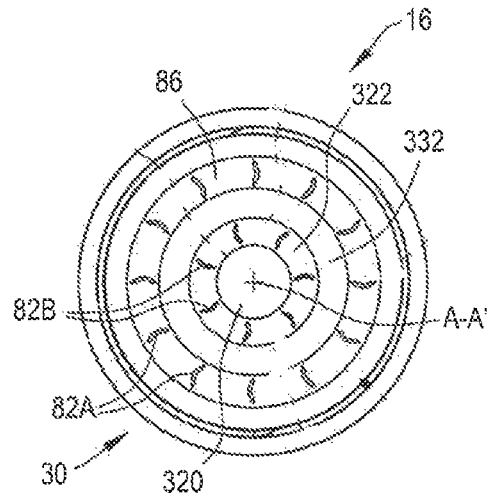

In another variant illustrated by FIG. 8, the application wall 30 delimits a first group of orifices 82A located radially outside a second group of orifices 82B.

The orifices 82A are distributed, for example, on an outer circumference of the application wall 30, whereas the orifices 82B of the second group are distributed on an inner circumference of the application wall 30.

Figure 9:
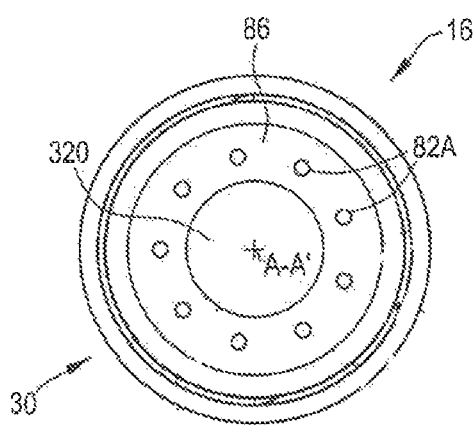

Another variant of the application head 16 is illustrated by FIG. 9. In this variant, the dispensing orifices 82A are formed by holes of circular or oblong cross section, and not by slits.

The maximum transverse dimension of each orifice 82A may be less than twice the minimum transverse dimension of the orifice 82A. Furthermore, at any point of each orifice, the smallest transverse dimension measured between two opposite edges of the orifice at this point is less than 3 mm, better still less than 1.3 mm and especially less than 1 mm. This smallest transverse dimension is advantageously between 0.4 mm and 0.8 mm and better still between 0.5 mm and 0.7 mm, for example equal to 0.6 mm. In other words, no orifice of the dispensing head comprises a point for which the smallest transverse dimension measured between two opposite edges of the orifice at this point is greater than 1.3 mm.

Figure 10:
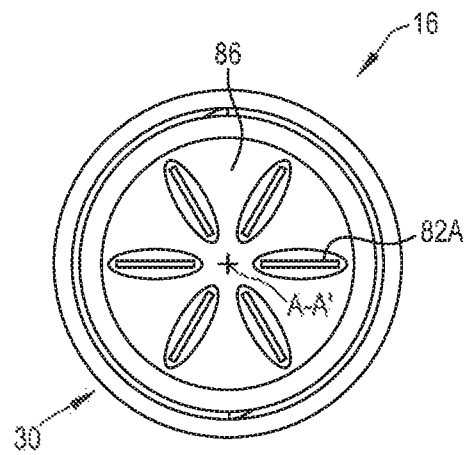

Yet another variant of the head 16 is illustrated by FIG. 10. In this variant, the dispensing orifices 82A are formed by slits extending radially relative to the centre of the applicator.

Generally, in all the embodiments, the total extent of the orifices 82A is less than 5% or even less than 2.5% of the total extent of the downstream surface 86 of the application wall 30.

The container with a deformable wall of the invention combined with a formulation of rheology described previously makes it possible to dispense a precise dose of the composition onto the application wall. Furthermore, it makes it possible to dispense the product with just one hand while at the same time applying the product to the skin.

The dimension of the dispensing orifices of the invention combined with a formulation of rheology described previously makes it possible to dispense a dose of the composition onto the application wall, by adjusting the desired amount in a precise manner by controlling the pressure generated on the container. Furthermore, with this combination, it is easier to dispense a specific dose of product by applying a substantially constant pressure in the container.

Furthermore, the dimension of the dispensing orifices combined with a formulation of rheology described previously limits the phenomenon of suction of the dose of product dispensed onto the application wall into the tube when the pressure in the so container is released.

Finally, the application wall is particularly suited to distributing and spreading the composition of the invention onto the skin while at the same time conserving an immediate dry, soft, non-wetting and non-tacky feel.

EXAMPLES

The examples were prepared according to the following protocol:
- the aqueous phase containing the gelling agents or thickeners and the aluminium salts is heated to 80° C.;
- the waxes and the surfactant mixture are heated with the oils to 80° C.;
- the two phases are mixed together and sheared in a Rayneri blender for 10 minutes;
- the filler is then added while mixing with a Rayneri deflocculator;
- the formulation is cooled to room temperature while mixing with a Rayneri deflocculator, before being conditioned.

Examples 1 to 3: Influence of the Choice of the Wax

| Phase | Ingredients | Example 1 (invention) | Comparative Example 2 with carnauba wax | Comparative Example 3 with ozokerite wax |
|---|---|---|---|---|
| A | Arachidylglucoside/behenyl alcohol and arachidyl alcohol (Montanov 202) | 3 | 3 | 3 |
| | Isopropyl palmitate (Dub IPP) | 10 | 11.5 | 10 |
| | Dimethicone (10 cSt) (Element14 PDMS 10-A) | 10 | 11.5 | 10 |
| | Beeswax White beeswax (GR B 889) | 3 | — | — |
| | Carnauba wax | — | 3 | — |
| | Ozokerite (Ozokerite Wax Pastilles SP 1021-P) | — | — | 3 |
| B | Hydroxypropyl starch phosphate (Structure XL) | 1 | 1 | 1 |
| | Steareth-100/PEG-136/HDI Copolymer (Rheolate FX 1100) | 0.5 | 0.5 | 0.5 |
| | Aluminium chlorohydrate as a 50% solution (Chlorohydrol 50) | 20 | 20 | 20 |
| | Water | qs 100 | qs 100 | qs 100 |

-continued

| Phase | Ingredients | Example 1 (invention) | Comparative Example 2 with carnauba wax | Comparative Example 3 with ozokerite wax |
|---|---|---|---|---|
| C | Silica (Sunsphere H 51) | 3 | 3 | 3 |
| | Viscosity: M3 - 200 s$^{-1}$ | 2600 mPa·s | Not measurable | 825 mPa·s |
| | Stability after 24 hours at 25° C. | Stable | Creaming | Sparingly thick cream |

The following were compared:
a formulation 1 according to the invention comprising, as wax, beeswax with a melting point of 62° C. and a content of ester containing at least 40 carbon atoms of 71% by weight;
a formulation 2 outside the invention comprising esters containing less than 30 carbons;
a formulation 3 outside the invention comprising ozokerite free of ester.

The results showed that formulation 1 according to the invention comprising beeswax has a thick cream appearance and remains stable after 24 hours at 25° C., unlike formulation 2 comprising an ester containing less than 30 carbons and formulation 3 with ozokerite.

Examples 4 to 6: Influence of the Choice of the Nonionic Surfactant/Fatty Alcohol Mixture

| Phase | Ingredients | Example 4 (invention) | Example 5 (invention) | Comparative Example 6 |
|---|---|---|---|---|
| A | Arachidylglucoside/ behenyl alcohol and arachidyl alcohol (Montanov 202) | 3 | — | — |
| | Cetylstearylglucoside/ cetylstearyl alcohol Montanov 68 | — | 3 | — |
| | C$_{14}$-C$_{22}$ alcohol/ C$_{12}$-C$_{20}$ alkylpolyglucoside (Montanov L) | — | — | 3 |
| | Dimethicone (10 cSt) (Element14 PDMS 10-A) | 10 | 10 | 10 |
| | Isopropyl palmitate (Dub IPP) | 10 | 10 | 10 |
| | Beeswax White beeswax (GR B 889) | 3 | 3 | 3 |
| B | Hydroxypropyl starch phosphate Structure XL | 1 | 1 | 1 |
| | Steareth-100/PEG-136/HDI Copolymer Rheolate FX 1100 | 0.5 | 0.5 | 0.5 |
| | Aluminium chlorohydrate as a 50% solution (Chlorohydrol 50) | 20 | 20 | 20 |
| | Water | qs 100 | qs 100 | qs 100 |
| C | Silica (Sunsphere H 51) | 3 | 3 | 3 |
| | Viscosity: M3 - 200 s$^{-1}$ | 2600 mPa·s | 1940 mPa·s | 1150 mPa·s |
| | Stability after 24 hours at 25° C. | Stable | Stable | Slight creaming 24 hours |

Examples 4 to 6 were prepared under the same conditions as Examples 1 to 3 and their stability was controlled according to the method indicated in the same examples.

Formulations 4 and 5 according to the invention, comprising, as mixture of surfactant/fatty alcohol containing an alkyl chain of greater than or equal to C$_{16}$, Montanov 202 and Montanov 68, were compared with a formulation 6 outside the invention, comprising a surfactant/fatty alcohol mixture, Montanov L comprising compounds containing an alkyl chain of less than C$_{16}$.

The results showed that formulations 4 and 5 according to the invention comprising Montanov 202 and Montanov 68 have a thick cream appearance and remain stable after 24 hours at 25° C., unlike formulation 6 comprising Montanov L, which shows creaming at 24 hours.

Examples 7 to 8: Influence of the Choice of Oils

| Phase | Ingredients | Comparative Example 7 with silicone oil | Example 8 (invention) |
|---|---|---|---|
| A | Arachidylglucoside/ behenyl alcohol and arachidyl alcohol (Montanov 202) | 3 | 3 |
| | Dimethicone (10 cSt) (Element14 PDMS 10-A) | 20 | — |
| | Isopropyl palmitate (Dub IPP) | — | 10 |
| | Hydrogenated polydecene (Silkflo 366 NF Polydecene) | — | 10 |
| | Beeswax White beeswax (GR B 889) | 3 | 3 |
| B | Hydroxypropyl starch phosphate (Structure XL) | 1 | 1 |
| | Steareth-100/PEG-136/HDI Copolymer (Rheolate FX 1100) | 0.5 | 0.5 |
| | Aluminium chlorohydrate as a 50% solution (Chlorohydrol 50) | 20 | 20 |
| | Water | qs 100 | qs 100 |
| C | Silica (Sunsphere H 51) | 3 | 3 |
| | Viscosity: M3 - 200 s$^{-1}$ | Not measurable | 2640 mPa·s |
| | Stability after 24 hours at 25° C. | Very fluid, presence of grains | Stable |

Examples 7 and 8 were prepared under the same conditions as Examples 1 to 3 and their stability was controlled according to the method indicated in the same examples.

Formulation 8 according to the invention, comprising, as oil phase, a mixture of hydrocarbon-based oils, was compared with a formulation 7 outside the invention comprising, as oil phase, a silicone oil.

The results showed that formulation 8 according to the invention comprising, as oil phase, a mixture of hydrocarbon-based oils has a thick cream appearance and remains stable after 24 hours at 25° C., unlike formulation 7 comprising, as oil phase, a silicone oil.

Examples 9 to 10: Influence of the Water-Soluble Polysaccharide

| Phase | Ingredients | Example 9 (invention) | Comparative Example 10 without starch |
|---|---|---|---|
| A | Arachidylglucoside/ behenyl alcohol and arachidyl alcohol (Montanov 202) | 3 | 3 |
|  | Dimethicone (10 cSt) (Element14 PDMS 10-A) | 10 | 10 |
|  | Isopropyl palmitate (Dub IPP) | 10 | 10 |
|  | Beeswax White beeswax (GR B 889) | 3 | 3 |
| B | Hydroxypropyl starch phosphate (Structure ZEA) | 1 | — |
|  | Steareth-100/PEG-136/HDI Copolymer (Rheolate FX 1100) | 0.5 | 0.5 |
|  | Water | qs 100 | qs 100 |
| Viscosity: M3 - 200 s$^{-1}$ |  | 2160 mPa · s | Not measurable |
| Stability after 24 hours at 25° C. |  | Stable | Fluid, non-uniform formulation |

Examples 9 and 10 were prepared under the same conditions as Examples 1 to 3 and their stability was controlled according to the method indicated in the same examples. Formulation 9 according to the invention comprising a water-soluble polysaccharide, Structure ZEA, was compared with a formulation 10 outside the invention free of water-soluble polysaccharide. The results showed that formulation 9 according to the invention comprising Structure ZEA has a thick cream appearance and remains stable after 24 hours at 25° C., unlike formulation 10 free of water-soluble polysaccharide, which remains fluid and non-uniform.

| Phase | Ingrédients | Example 11 (outside the invention) |
|---|---|---|
| A | BEHENYL GLYCOSIDE/ALCOOL BEHENYLIQUE (MONTANOV 202 ®) | 3 |
|  | DIMETHICONE (10 CST) (ELEMENT14 PDMS 10-A ®) | 10 |
|  | ISOPROPYL PALMITATE (DUB IPP ®) | 10 |
|  | C20-C40 ALKYL STEARATE KESTERWACHS | 3 |
| B | HYDROXYPROPYL STARCH PHOSPHATE (STRUCTURE XL ®) | 1 |
|  | STEARETH-100/PEG-136/HDI COPOLYMER (RHEOLATE FX 1100 ®) | 0.5 |
|  | ALUMINUM CHLOROHYDRATE EN SOLUTION A 50% (CHLORHYDROL 50) | 20 |
|  | PRESERVATIVES | 0.6 |
|  | WATER | qsp 100 |
| C | SILICA (SUNSPHERE H 51 ®) | 3 |

Example 11 was prepared under the same conditions as Examples 1 to 3.

A sensorial test was made on a panel of 11 persons according to the criteria of freshness onto the skin after application and the speed of penetration of the product. Each criteria was noted between 1 to 3.

Example 9 according to the invention of identical composition but comprising bee wax instead of the C20-C40 alkyl stearate kesterwachs was compared to example 11.

Freshness: 1=unfresh and 3=very fresh

Speed of penetration: 1=very slow penetration and 3=very fast penetration 7 persons on 11 estimated the product 9 very fresh with a very fast penetration on contrast with example 11.

Example 12 was prepared under the same conditions as Examples 1 to 3.

| Phase | Ingrédients | Example 12 (outside the invention) |
|---|---|---|
| A | BEHENYL GLYCOSIDE/ ALCOOL BEHENYLIQUE (MONTANOV 202 ®) | 3 |
|  | DIMETHICONE (10 CST) (ELEMENT14 PDMS 10-A ®) | 10 |
|  | ISOPROPYL PALMITATE (DUB IPP ®) | 10 |
|  | POLYETHYLENE WAX (CIREBELLE 108 ®) | 3 |
| B | HYDROXYPROPYL STARCH PHOSPHATE (STRUCTURE XL ®) | 1 |
|  | STEARETH-100/PEG-136/HDI COPOLYMER (RHEOLATE FX 1100 ®) | 0.5 |
|  | ALUMINUM CHLOROHYDRATE EN SOLUTION A 50% (CHLORHYDROL 50) | 20 |
|  | PRESERVATIVES | 0.6 |
|  | WATER | qsp 100 |
| C | SILICA (SUNSPHERE H 51 ®) | 3 |
| Viscosity: M3 - 200 s-1 |  | 690 mPa · s | Liquid composition |

| Phase | Ingredients | Example 13 (invention) | Example 14 (outside the invention) |
|---|---|---|---|
| A | C14-C22 ALCOOL/ C12-C20 ALKYLPOLYGLUCOSIDE (MONTANOV L ®) | 3 | 3 |
|  | DIMETHICONE (10 CST) (ELEMENT14 PDMS 10-A ®) | 10 | 10 |
|  | ISOPROPYL PALMITATE (DUB IPP ®) | 10 | 10 |
|  | *EUPHORBIA CERIFERA* (CANDELILLA) WAX (CANDELILLA WAX SP 75 G ®) | 3 | 0.6 |
| B | HYDROXYPROPYL STARCH PHOSPHATE (STRUCTURE XL ®) | 1 | 1 |
|  | STEARETH-100/PEG-136/HDI COPOLYMER (RHEOLATE FX 1100 ®) | 0.5 | 0.5 |
|  | ALUMINUM CHLOROHYDRATE EN SOLUTION A 50% (CHLORHYDROL 50) | 20 | 20 |
|  | CONSERVATEUR | 0.075 | 0.075 |
|  | EAU | qsp 100 | qsp 100 |

-continued

| Phase | Ingredients | Example 13 (invention) | Example 14 (outside the invention) |
|---|---|---|---|
| C | SILICA (SUNSPHERE H 51 ®) | 3 | 3 |
| | Viscosity: M3 - 200 s-1 | 2700-2790 m Pa · s | 1020-1060 m Pa · s |
| | Stability after 24 hours at 25° C. | Stable | Creaming after 24 hours and decantation of the silica |

Examples 13 and 14 were prepared under the same conditions as Examples 1 to 3 and their stability was controlled according to the method indicated in the same Examples 1 to 3. The results showed that Example 13 of the invention comprising Candelilla Wax at 3% by weight has a thick cream appearance and remains stable after 24 hours at 25° C., unlike formulation 14 comprising Candelilla Wax in an amount less than 1% by weight (0.6%).

Example 15 was prepared under the same conditions as Examples 1 to 3.

| Ingredients | Example 15 according to example 4 of EP2436369 (outside the invention) |
|---|---|
| WATER | qsp 100 |
| XANTHAN GUM | 0.05 |
| CARBOMER | 0.10 |
| GLYCERIN | 3.00 |
| BUTYLENE GLYCOL | 8.00 |
| PHENOXYETHANOL | 0.50 |
| SODIUM CITRATE | 0.09 |
| POLYVINYL ALCOHOL | 0.20 |
| SODIUM METHYL COCOYL TAURATE | 0.20 |
| CITRIC ACID | 0.01 |
| GLYCERYL STEARATE SE | 0.30 |
| DIMETHICONE | 1.00 |
| AERYTHRITYL TETRAETHYLHEXANOATE | 2.00 |
| MINERAL OIL | 4.50 |
| EIS GUINEENSIS (PALM) OIL | 0.50 |
| BEHENYL ALCOHOL | 0.80 |
| CANDELLILA WAX | 0.20 |
| MICROCRYSTALLINE WAX | 0.08 |
| POLYETHYLENE WAX | 0.32 |
| Viscosity: M3 - 200 s-1 | 200-350 mPa · s |

The invention claimed is:

1. A composition in the form of an oil-in-water emulsion comprising, in a cosmetically acceptable medium:
   A) a continuous aqueous phase in an amount from 50% to 90% by weight based upon the total weight of the composition and
   B) an oily phase dispersed in the said aqueous phase in an amount from 10% to 30% by weight based upon the total weight of the composition and comprising at least one hydrocarbon-based oil;
   C) at least one mixture in an amount from 1% to 10% by weight based upon the total weight of the composition of:
      (i) at least one nonionic surfactant containing a saturated linear hydrocarbon-based chain comprising at least 16 carbon atoms, the said surfactant being other than a fatty alcohol, and
      ii) at least one fatty alcohol in pure form containing at least 16 carbon atoms or a mixture of fatty alcohols containing at least 16 carbon atoms;
   D) 10% to 30% by weight based upon the total weight of the composition of at least one wax with a melting point of greater than 45° C. comprising one or more $C_{40}$-$C_{70}$ ester compounds, in an amount from 1 to 10% by weight relative to the total weight of the composition and
   E) at least one water-soluble polysaccharide in an amount from 0.5% to 6% by weight based upon the total weight of the composition; the said composition having a viscosity, measured at 25° C. with a Rheomat RM 180 viscometer at 200 $s^{-1}$ at room temperature with a No. 3 or No. 4 spindle after 10 minutes, ranging from 1500 mPa·s to 12 000 mPa·s.

2. The composition according to claim 1, wherein the at least one nonionic surfactant is selected from the group consisting of:
   alkylpolyglucosides in which the alkyl chain comprises at least 16 carbon atoms;
   ethoxylated fatty alcohols comprising at least 16 carbon atoms; and
   polyglyceryl fatty esters containing a chain comprising at least 16 carbon atoms;
   mixtures thereof.

3. The composition according to claim 1, wherein the at least one nonionic surfactant is chosen from alkylpolyglycosides.

4. The composition according to claim 1, in which the at least one fatty alcohol is selected from the group consisting of:
   (i) the following pure fatty alcohols: cetyl alcohol, stearyl alcohol, behenyl alcohol, arachidyl alcohol, and mixtures thereof; and
   (ii) the following mixtures of fatty alcohols:
      a cetearyl alcohol mixture,
      mixtures based on at least one $C_{22}$ fatty alcohol, at least one $C_{20}$ fatty alcohol and at least one $C_{18}$ fatty alcohol, and
      a mixture of behenyl alcohol and arachidyl alcohol.

5. The composition according to claim 1, wherein the mixture of the at least one nonionic surfactant and of the at least one fatty alcohol is selected from the group consisting of:
   a mixture of arachidyl alcohol, behenyl alcohol and arachidylglucoside;
   a mixture of cetearyl alcohol and cetearylglucoside;
   and mixtures thereof.

6. The composition according to claim 1, wherein the wax is selected from the group consisting of candelilla wax, rice bran wax, beeswax and sunflower wax, and mixtures thereof.

7. The composition according to claim 1, wherein the oily phase comprises at least one non-volatile hydrocarbon-based oil and optionally at least one non-volatile silicone oil.

8. The composition according to claim 7, in which the hydrocarbon-based oil is chosen from triglycerides, fatty acid esters, alkanes, and mixtures thereof.

9. The composition according to claim 1, wherein the concentration of the oily phase ranges from 10% to 20% relative to the total weight of the composition and the concentration of the aqueous phase ranges from 60% to 90% by weight relative to the total weight of the composition.

10. The composition according to claim 1, wherein the water-soluble polysaccharide is chosen from starches.

11. The composition according to claim 10, in which the starch is a distarch phosphate.

12. The composition according to claim 1, wherein the at least one hydrocarbon-based oil is present at concentrations ranging from 5% to 30% by weight relative to the total weight of the composition.

13. The composition according to claim 1, wherein the at least one wax with a melting point of greater than 45° C. comprising one or more $C_{40}$-$C_{70}$ ester compounds represents from 2 to 8% by weight relative to the total weight of the composition.

14. The composition according to claim 1, which also comprises at least one nonionic associative polymer.

15. The composition according to claim 1, which also comprises at least one antiperspirant active agent and/or one deodorant active agent.

16. A cosmetic process for treating and/or caring for human keratin materials, which comprises applying to the surface of the keratin material a composition as defined in claim 1.

17. A cosmetic process for treating human perspiration and/or perspiration-related body odour, which comprises applying to the surface of a human keratin material a composition as defined in claim 15.

18. A dispensing device, which comprises:
a container comprising a deformable wall
a composition according to claim 1, stored in the container, and
a dispensing head closing off the container and comprising an application wall defining at least one product dispensing orifice.

19. A device according to claim 18 wherein the application wall is formed from a thermoplastic elastomer.

20. The composition according to claim 1, wherein the at least one nonionic surfactant is chosen from alkylpolyglycosides;
the at least one fatty alcohol is selected from the group consisting of:
(i) the following pure fatty alcohols: cetyl alcohol, stearyl alcohol, behenyl alcohol, arachidyl alcohol, and mixtures thereof; and
(ii) the following mixtures of fatty alcohols:
a cetearyl alcohol mixture,
mixtures based on at least one $C_{22}$ fatty alcohol, at least one $C_{20}$ fatty alcohol and at least one $C_{18}$ fatty alcohol, and
a mixture of behenyl alcohol and arachidyl alcohol; and
the wax is selected from the group consisting of candelilla wax, rice bran wax, beeswax and sunflower wax, and mixtures thereof.

21. The composition according to claim 20, wherein the at least one fatty alcohol is selected from the group consisting of:
the following mixtures of fatty alcohols:
a cetearyl alcohol mixture,
mixtures based on at least one $C_{22}$ fatty alcohol, at least one $C_{20}$ fatty alcohol and at least one $C_{18}$ fatty alcohol, and
a mixture of behenyl alcohol and arachidyl alcohol; and
the wax is selected from the group consisting of candelilla wax and beeswax, and mixtures thereof.

* * * * *